United States Patent [19]

Nelson

[11] 4,386,202

[45] May 31, 1983

[54] CHLOROAMMELIDES AND THEIR PREPARATION

[75] Inventor: George D. Nelson, Creve Coeur, Mo.

[73] Assignee: Monsanto Company, St. Louis, Mo.

[21] Appl. No.: 270,677

[22] Filed: Jun. 5, 1981

[51] Int. Cl.³ .......................................... C07D 251/46
[52] U.S. Cl. ................................................... 544/194
[58] Field of Search ........................................ 544/194

[56] References Cited

U.S. PATENT DOCUMENTS 2,184,886 12/1939 Muskat et al. ..................... 260/248
4,122,268 10/1978 Berkowitz ........................... 544/194

OTHER PUBLICATIONS

Potashnik et al., Chemical Abstracts, vol. 70, Entry 47507 (1969).
Verkholetova et al., *Tr. Tsent. Nauch-Issled Denzinfek Inst.*, vol. 19, pp. 128–134 (1970), English Translation.

*Primary Examiner*—John M. Ford
*Attorney, Agent, or Firm*—Jon H. Beusen; James C. Logomasini; William H. Duffey

[57] ABSTRACT

Compounds containing a chloroammelide moiety having the formula

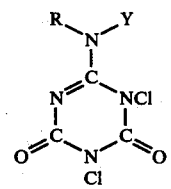

wherein R is alkali metal or H, Y is Cl or H, and Y is H when R is H, said compounds being not fully hydrated when R is alkali metal, contain both free and combined chlorine, and are attractive for use in bleaching. Those not fully hydrated can be prepared by removing combined water of hydration from more fully hydrated compounds obtained by chlorinating an aqueous mixture of ammelide and alkali metal ions. The fully hydrated compound wherein R is H is prepared by chlorinating an aqueous mixture of ammelide and about 2–2.2 moles of alkali metal ion per mole of ammelide.

20 Claims, No Drawings

CHLOROAMMELIDES AND THEIR PREPARATION

BACKGROUND OF THE INVENTION

Various N-chloro heterocyclic compounds have been synthesized with the object of providing sources of available chlorine for bleaching and/or sanitizing. For example, various chlorinated s-triazine triones which are highly effective in such uses are manufactured and sold by Monsanto Company under the trademark ACL® sanitizer and bleaching compounds. In those compounds, a high proportion of the available chlorine is free (hypochlorous) chlorine which is critically important for sanitizing uses, e.g. in swimming pool disinfectants. For certain other uses, e.g. bleaching of cloth, it is highly desirable to use N-chloro compounds containing available chlorine which includes combined (chloramine) chlorine in addition to such free chlorine. In those uses, the combined chlorine has the advantage that it is released more slowly and hence has less of a tendency to damage delicate fabrics, fabric colors, etc.

Accordingly, it is an object of this invention to provide a class of novel N-chloro heterocyclic compounds containing available chlorine. Another object is a class of such compounds containing both free chlorine and combined chlorine. Another object is a class of such compounds containing free and combined chlorine in relatively high proportions. Another object is a class of such compounds having good stability at temperatures encountered in normal end uses, storage and/or transportation. Other objects include convenient processes for the preparation of such compounds. These and other objects will be more readily apparent from this disclosure, in which all percentages are by weight and all temperatures are in degrees Celsius, except where otherwise noted. Also in this disclosure, the term "hydrated" is used to indicate that a compound contains combined water of hydration, and the term "anhydrous" indicates that a compound does not contain combined water of hydration.

SUMMARY OF THE INVENTION

Each of the novel compounds of this invention contains a chloroammelide moiety having the structural formula

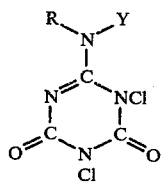

wherein R is alkali metal or H, Y is Cl or H, and Y is H when R is H. Included in the invention are each of the anhydrous and hydrated compounds containing such a chloroammelide moiety, except that such compounds are not fully hydrated when R is alkali metal.

Also provided by this invention is a process for preparing such compounds which are not fully hydrated, by contacting an aqueous mixture of ammelide and alkali metal ions with chlorine under conditions resulting in formation of a compound containing a chloroammelide moiety having the foregoing formula, and then removing combined water of hydration from said compound without causing substantial decomposition of that moiety. In another embodiment of such a process, a compound containing a chloroammelide moiety having the foregoing formula and combined water of hydration is heated to a temperature sufficient to remove combined water of hydration from that compound without causing such decomposition.

Also provided is a process for preparing a compound containing a chloroammelide moiety having the structural formula

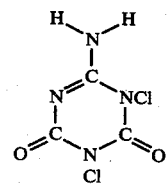

and one mole of combined water of hydration per mole of that compound, by contacting an aqueous solution of ammelide and between about 2 and about 2.2 moles of alkali metal hydroxide per mole of said ammelide at a temperature between about 5° and about 30° with sufficient chlorine to form said compound.

PRIOR ART

U.S. Pat. No. 2,184,886 issued Dec. 26, 1939 to I. E. Muskat et al discloses that chlorinating ammelide, optionally from the beginning in the presence of an alkali metal hydroxide, results in solid products of chemical structures said to be unknown.

According to 70 Chemical Abstracts 47507 (1969), Russian Pat. No. 226,625 issued Sept. 16, 1968 to A. A. Potashnik et al discloses chlorinating ammelide in the presence of an alkali metal hydroxide. From the elemental analysis reported in that patent, it appears the product was trichloroammelide rather than an alkali metal salt of a chloroammelide.

G. P. Verkholetova et al, "Synthesis of Chlorine-Active Preparations From Waste Products of the Production of Cyanuric Acid", 19 Tr. Tsent. Nauch-Issled Dezinfek Inst. 128–34 (1970), discloses chlorinating alkaline solutions of ammelide-containing mixtures which are intermediates in or waste products from the production of cyanuric acid, and reports that the chlorinated mixtures (identified as consisting of dichloroisocyanuric acid, trichloroammelide and dichloroammeline) soften but do not melt between 208° and 212°. The article mentions preparation of potassium salts of such chlorinated mixtures (and trichloroammelide separately) but does not describe a procedure therefor.

U.S. Pat. No. 4,122,268 issued Oct. 24, 1978 to S. Berkowitz discloses chlorinating ammelide in the presence of NaOH sufficient to neutralize byproduct HCl as well as result in a 2.0–4.5 pH on completion of the reaction. Duplications of the specific process example in that patent have provided sodium trichloroammelide, rather than the tetrachloroammelide reported in that example.

DETAILED DESCRIPTION OF THE INVENTION

The compounds of this invention are normally solid and form free-flowing crystals which are dry (essentially free of surface moisture) in equilibrium with the atmosphere under standard conditions of temperature, pressure and humidity. Such compounds, and the crystalline forms thereof, have good stability at temperatures normally encountered in transportation and/or storage. All of such compounds are useful in bleaching of textile materials containing natural (e.g. cellulosic) or synthetic fibers or combinations thereof, and are especially attractive for use with delicate and/or colored fabrics because a substantial proportion of their chlorine is combined (rather than free) and therefore has less tendency to damage fiber structure or color.

In the structural formula of the compounds disclosed herein, R is hydrogen or alkali metal, i.e., a metal from the first group of the Periodic Table of the Elements. For most uses of such compounds, R is preferably sodium, potassium or lithium, and even more preferably sodium or potassium. In the same formula, Y is chlorine or hydrogen. When R in that formula is hydrogen, Y is also hydrogen.

An important distinguishing feature of such compounds has to do with the absence or presence of combined water of hydration, i.e., water of crystallization that is molecularly combined with such a compound in an integral number of moles per mole of that compound, and not merely trapped within crystals of such a compound. Thus, each compound of this invention has an X-ray diffraction pattern distinctly different from those of its counterparts having the same chloroammelide moiety but greater or fewer (including zero) moles of combined water of hydration per mole of that compound.

In various important respects, the compounds of this invention which are not fully hydrated are more stable than their fully hydrated counterparts. For example, at temperatures normally encountered in storage or transportation, the compounds which are not fully hydrated are more resistant to caking, reactive rearrangement or decomposition, etc. In addition, the compounds which are not fully hydrated have lower shipping weights than their fully hydrated counterparts.

Each compound of this invention which is not fully hydrated can be prepared by removing combined water of hydration from its fully hydrated counterpart, i.e., the compound having the same chloroammelide moiety and the number of moles of combined water of hydration which result when that compound precipitates from aqueous solution at a temperature of 15°. Heretofore, it has not been recognized that such compounds contain combined water of hydration, let alone that removal of such water of hydration can be conveniently controlled to provide each corresponding chloroammelide having combined water of hydration in any desired integral number of moles (including zero) which is less than that of its fully hydrated counterpart.

More specifically, it has been discovered that sodium trichloroammelide precipitates from such aqueous media as its tetrahydrate which, in accordance with this invention, can be fully or partially dehydrated to provide each of its lower hydrates having three, two or one mole of combined water of hydration per mole of the sodium trichloroammelide or, alternatively, anhydrous sodium trichloroammelide. Similarly, sodium dichloroammelide precipitates as its dihydrate, which can be dehydrated to the corresponding monohydrate (one mole of combined water of hydration per mole of sodium dichloroammelide) or anhydrous sodium dichloroammelide. Potassium trichloro- and dichloroammelides and unneutralized dichloroammelide precipitate as their respective monohydrates (one mole of combined water of hydration per mole of each of those compounds) which can be dehydrated to the corresponding anhydrous compounds.

In general, the most convenient method for removing such water of hydration is by heating the hydrated compounds to an elevated temperature sufficient to effect the desired degree of dehydration. Temperatures suitable for use in preparing each of the aforementioned not-fully-hydrated compounds are disclosed in the specific examples herein. Alternatively, the water can be removed by other techniques such as, e.g. low-pressure drying, solvent evaporation, or use of a suitable dehydrating agent (e.g. P2O5).

Although other procedures can be used, it is generally convenient to prepare the aforementioned fully hydrated compounds by chlorinating an aqueous mixture of ammelide and alkali metal ions. Typically gaseous chlorine is employed, but other sources of the required chlorine atoms can be used (e.g., hypochlorites). The ammelide can be introduced to the aqueous mixture as unsubstituted ammelide, an alkali metal salt thereof, a chloroammelide, or any other source of suitably reactive ammelide ions. The alkali metal ions are provided preferably by addition of alkali metal hydroxide, but other noninterfering alkali metal compounds (e.g., carbonates) can be used. Mole ratios of the ammelide, alkali metal and chlorine are adjusted to obtain the desired reaction product. Typically, the mixture includes sufficient water to provide reactive ammelide and alkali metal ions, furnish the water of hydration in the precipitated chloroammelides and provide a suitable environment for precipitation of such reaction products. However, it is believed that such precipitation, if carried out at a temperature effective in partially dehydrating the fully hydrated chloroammelide, will provide the corresponding lower hydrate which may be used, if desired, in the preparation of still lower hydrates in accordance with this invention.

An exemplary synthesis of such a fully hydrated chloroammelide is the aforedescribed process for preparing the monohydrate of dichloroammelide, which process comprises contacting a mixture of ammelide, between about 2 and about 2.2 (preferably between about 2.05 and about 2.1) moles of alkali metal ion per mole of said ammelide, and water sufficient to dissolve such reactants (preferably between about 8 and about 30 moles of water per mole of the ammelide) with sufficient chlorine to form the desired product. Normally when such chlorination is complete, the pH of the solution has been lowered to between about 2 and about 3. Like the analogous preparations of other chloroammelides useful in the process of this invention, this chlorination is carried out preferably between about 5° and about 30°, and usually even more advantageously between about 10° and about 20°.

Further information about preparation of the aforementioned fully hydrated salts of trichloro- and dichloroammelide may be found in U.S. Pat. Nos. 2,184,886 and 4,122,268, the disclosures of which are incorporated herein by reference. Heretofore, such compounds have been generally prepared by contacting an aqueous mixture of ammelide and alkali metal ions with chlorine beginning at a strongly alkaline pH (e.g., about 13) and continuing until the mixture pH is lowered below about 3. However, it has now been found that carrying out such contacting essentially completely (throughout the reaction) at a pH between about 2 and about 7, even more preferably between about 2 and about 3, satisfactorily provides the same product with the further advantages of permitting a continuous, steady-state operation and, in some cases, resulting in less decomposition of the ammelide reactant.

In another variation of the prior art process, additional base can be included in the reaction mixture so that the desired compound is formed before the pH of the mixture declines below about 6. In this variation, in which a pH of at least about 6 is maintained essentially throughout the chlorination reaction, the hydrated chloroammelide precipitates as it is formed, avoiding decomposition which would otherwise result from exposure to continued chlorination.

In another variation of the process, alkali metal salts of dichloroammelide can be prepared by mixing preformed dichloroammelide with an aqueous solution of alkali metal ions. This process is easily controlled and, because the solubility of the desired salt is lower than that of dichloroammelide with a slight excess of alkali metal ions present, product precipitation/filtration can be carried out continuously, leaving a filtrate suitable for recycle.

In still another variation of the process useful in preparing alkali metal salts of dichloroammelide, a mixture of two moles of trichloroammelide and about one mole of unsubstituted ammelide is contacted with an aqueous solution containing about three moles of alkali metal ion. This can be carried out in aqueous solution or in the presence of water insufficient to completely dissolve the mixture but sufficient to initiate the reaction and provide the desired hydrated product. Advantages of the slurry process are that the ammelides are essentially 100% converted, less drying is required, and there is no filtrate.

Following preparation of a hydrated chloroammelide by any of the procedures just described, the hydrated compound is normally separated from the aqueous mixture in which it has been prepared, e.g., by precipitation as a solid. Preferably such precipitation is followed by filtration or centrifuging, leaving a mass of crystals having typically from about 15% to about 40% of superficial (chemically uncombined) water which can be removed by any suitable technique (e.g., evaporation). Generally such superficial water must be removed before removal of the combined water of hydration can be completed or, in some cases, even substantially begun. Whether or not dehydration of such a hydrated compound is begun in the presence of superficial water, removal of the combined water of hydration is usually most easily accomplished by heating such compounds to elevated temperatures, preferably without substantial decomposition of the chloroammelide moiety of the compound. In this context, decomposition which is not substantial is not greater than about 10%, and preferably not greater than about 5% of the compound undergoing such dehydration. Isomerizations of the chloroammelide moiety (e.g. to its enol form) are not to be considered decomposition of that moiety.

In general, the removal of superficial water and/or combined water of hydration is conveniently carried out with use of an air stream flash dryer as described on pages 242–51 of ENCYCLOPEDIA OF CHEMICAL PROCESS EQUIPMENT by William J. Mead, Reinhold Publishing Corporation, New York, N.Y. (1964), the disclosure of which is incorporated herein by reference. However, other procedures such as, e.g., the use of a rotary dryer or drying oven (preferably with circulating air) can be used. In some instances, it has been observed that even after substantially complete removal of superficial water, compounds of this invention may temporarily redissolve in their own water of hydration during its removal from such compounds.

Various of such compounds are described in the following examples which are illustrative only and do not imply any limitations on the scope of the invention. Free, combined and available (total) chlorine in the compounds of these examples are defined and were determined amperometrically in accordance with ASTM Method D1253-68, and the percentages of available (total) chlorine were checked iodometrically by thiosulfate titrations. Filtrations were carried out using No. 1 Whatman paper on a three-inch Buchner funnel.

Preparation of Ammelide

Ammelide used in the following syntheses of compounds of this invention was prepared by dissolving one mole (184.4 g) of cyanuric chloride in one liter of acetone, lowering temperature of the solution to −20°, and then adding 34 g of anhydrous ammonia at a rate which kept the solution temperature below 0°. When the reaction was complete, the mixture was poured over crushed ice, and the solids were filtered off when the ice melted. After the remaining material was reslurried in three liters of water, its pH was adjusted to 1.5–2.0 and its temperature was raised to about 80° for 30 minutes to hydrolyze the remaining chlorine atoms on the cyanuric chloride ring. The yield (123 g) was about 96% of theoretical. By gas chromatography, the product was found to be 98+% ammelide.

EXAMPLE 1

Sodium Trichloroammelide 12.8 g of the 98+% ammelide was suspended in a solution of 16.2 g (0.404 moles) of NaOH in 300 ml of water. The resulting slurry was cooled to 5°–10° C. and 30 g of gaseous chlorine was bubbled through it with stirring until its pH declined from 14 to 2.9. The yellow crystals which formed were separated by filtration and dried at room temperature, producing a dry, free-flowing, yellow-white powder containing 64.7% available chlorine and 20.1% water of crystallization. Chemical analysis of the powder indicated a compound containing a chloroammelide moiety having the following structural formula and four moles of water of crystallization:

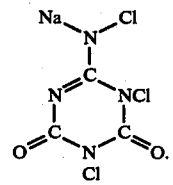

On heating the air-dried powder gradually to higher temperatures, differential thermal analyses (DTA) showed that from each mole of the sodium trichloroammelide product, four moles of combined water of hydration were removed, the first at 80°, the second at 90°, the third at 104° and the fourth at 118°. Analysis of the resulting product (a slightly yellow powder having a faint chlorine odor) indicated an anhydrous compound having the structural formula shown previously in this example and the following properties: 81.1% available chlorine (theoretical 84.0%) of which 67% was free and 33% was combined; melting point 158°;

decomposition temperature 165°; dissociation constant 1.26×10⁻¹⁰; pK 9.9; 1% solubility in water at 25°; 4.65 pH of that 1% solution.

EXAMPLE 2

Potassium Trichloroammelide 23.8 g of the 98+% ammelide was combined with 600 ml of water and 53.2 g of 85% KOH (45.2 g of anhydrous KOH equivalent), the mixture was cooled to 10° C., and gaseous chlorine was introduced with a sparger over one hour as the pH declined from about 14 to 3.5, when 43 g (0.61 moles) of chlorine had been added. The resulting yellow slurry with the consistency of cream was filtered, after which the crystals were washed with 100 ml of water in three doses and then dried in room temperature air to constant weight, providing a dry, free-flowing powder containing 72.5% available chlorine. Chemical analysis of the powder indicated a compound containing a chloroammelide moiety having the following structural formula and one mole of water of crystallization:

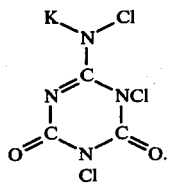

Using DTA, it was found that by gradually heating the powder to higher temperatures, a single mole of combined water of hydration was removed at 110°. Analysis of the resulting product (a cream-colored powder having a faint chlorine odor) indicated an anhydrous compound having the structural formula shown previously in this example and the following properties: 76.9% available chlorine (79.0% theoretical) of which 66% was free and 34% was combined; no melting point; decomposition temperature 175°; about 1% solubility in water at 25°; dissociation constant 1.905×10⁻¹⁰; pK 9.72.

EXAMPLE 3

Sodium Dichloroammelide 12.8 g of the 98+% ammelide and 12.18 g of NaOH were dissolved in 200 ml of water. 14 g of gaseous chlorine was bubbled through the resulting solution at 5° C. over 40 minutes during which the solution pH declined from 13.9 to 6.5. Precipitated crystals were separated by filtration and washed twice with a total of 20 ml of water. 13 g of the remaining wet cake was dried to constant weight (7.1 g) at room temperature. A second crop of 5.1 g of dried crystals was obtained by stirring 35 g of NaCl into the filtrate at 5° C., and then filtering and drying. Yield of this relatively soluble product was 58% of theoretical. The product was a dry, free-flowing, yellow-orange powder containing 55.6% available chlorine and 14% water of crystallization. Chemical analysis of the powder indicated a compound containing a chloroammelide moiety having the following structural formula and two moles of water of crystallization:

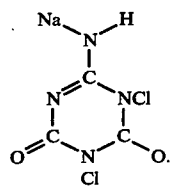

Using DTA, it was found that gradually heating this powder to higher temperatures resulted in the loss, based on one mole of the sodium dichloroammelide, of one mole of water at 72° and a second mole of water at 90° C. Analysis of the resulting product (an orange powder having a faint chlorine odor) indicated an anhydrous compound having the structural formula shown previously in this example and the following properties: 57.5% available chlorine (64.8% theoretical) of which about one-half was free and about one-half was combined; melting point 157°; decomposition temperature 175°; >1% solubility in water at 25°; 5.2 pH of a 1% solution in water; dissociation constant 1.58×10⁻¹⁰; pK 9.8.

EXAMPLE 4

Potassium Dichloroammelide

Initially, trichloroammelide was produced by bubbling 24 g of gaseous chlorine through a slurry of 12.8 g of the 98+% ammelide and 12.1 g of NaOH in 600 ml of water at 8°–15° C. (which lowered the pH of the slurry from 13.8 to 2.5), filtering the resulting white crystals from solution, washing the filtered crystals three times with 50 ml of water, and drying them at room temperature to constant weight (17.3 g; 75% of theoretical). Chemical analysis of the crystals indicated an anhydrous compound having the following structural formula:

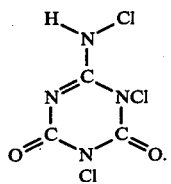

4.6 g of trichloroammelide prepared as just described and 1.3 g of the 98+% ammelide were dissolved in 100 ml of water at 40°. 45% KOH was added dropwise until the solution pH was about 8. 10 g of KCl was added and the solution was cooled to 5°. The resulting cream-colored, powdery crystals were separated by filtration and then dried at room temperature to constant weight (5.1 g; 75% of theoretical). Chemical analysis of the resulting dry, free-flowing powder indicated a compound containing a chloroammelide moiety having the following structural formula and one mole of water of crystallization:

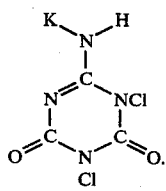

Using DTA, it was found that heating the crystals gradually to higher temperatures removed one mole of combined water of hydration per mole of the potassium dichloroammelide at 110° C. Analysis of the resulting product (a cream-colored powder having a faint chlorine odor) indicated an anhydrous compound having the structural formula shown previously in this example and the following properties: no melting point; decomposition temperature 195°; about 1% solubility in water at 25°; dissociation constant $2.09 \times 10^{-10}$; pK 9.68; 62.8% available chlorine (60.4 theoretical) of which about one-half was free and about one-half was combined.

EXAMPLE 5

Dichloroammelide 12.8 g of the 98+% ammelide and 8.08 g (0.202 moles) of NaOH in 250 ml of water were contacted with 15 g (0.21 moles) of gaseous chlorine at 5°–10° over 35 minutes, causing the pH of the solution to decline from 13 to 3. The resulting white crystals were filtered from the solution, washed three times with a total of 50 ml of water, and then dried at room temperature to constant weight (18.3 g; 93% of theoretical). The product was a dry, free-flowing, white powder containing 62% available chlorine (66.0% theoretical) and 8.6% water of crystallization. Chemical analysis of the powder indicated a compound containing a chloroammelide moiety having the following structural formula and one mole of water of crystallization:

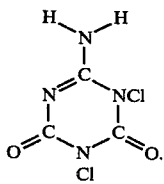

Using DTA, it was found that gradual heating of this powder to higher temperatures resulted in the loss at 87° of one mole of combined water of hydration per mole of the dichloroammelide. Analysis of the resulting product (a white powder having a faint chlorine odor) indicated an anhydrous compound having the structural formula shown previously in this example and the following properties: no melting point; decomposition temperature 218°; about 0.15% solubility in water at 25°; 2.7 pH of a 1% suspension; dissociation constants $3.16 \times 10^{-5}$ and $1.41 \times 10^{-10}$; pK's 4.5 and 9.85, respectively; 69.4% available chlorine (72.1% theoretical) of which 50% was free and 50% was combined. Hydrolysis of this product in the presence of $Na_2SO_3$ resulted in essentially complete conversion to ammelide, confirming that both chlorine atoms in the anhydrous compound were associated with nitrogen atoms in the ring rather than the nitrogen atom in the amine substituent on the ring.

I claim:
1. A compound having the structural formula

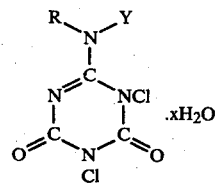

wherein R is alkali metal or H, Y is Cl or H, Y is H when R is H, and x represents the number of moles of water of hydration combined with each mole of said compound, x being zero or a positive integer, said compound being not fully hydrated.

2. A compound according to claim 1 wherein R is Na, Y is Cl and x is zero.
3. A compound according to claim 1 wherein R is Na, Y is Cl and x is one.
4. A compound according to claim 1 wherein R is Na, Y is Cl and x is two.
5. A compound according to claim 1 wherein R is Na, Y is Cl and x is three.
6. A compound according to claim 1 wherein R is Na, Y is H and x is zero.
7. A compound according to claim 1 wherein R is Na, Y is H and x is one.
8. A compound according to claim 1 wherein R is K, Y is Cl and x is zero.
9. A compound according to claim 1 wherein R is K, Y is H and x is zero.
10. A compound according to claim 1 wherein R is H and x is zero.
11. A process for preparing a compound containing a chloroammelide moiety having the structural formula

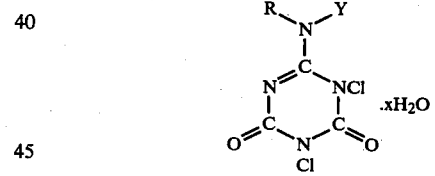

wherein R is alkali metal or H, Y is Cl or H, Y is H when R is H, and x represents the number of moles of water of hydration combined with each mole of said compound, x being zero or a positive integer, said compound being not fully hydrated, which process comprises contacting an aqueous mixture of ammelide and alkali metal ions with chlorine under conditions resulting in formation of a hydrated compound containing a chloroammelide moiety having said structural formula, and then removing combined water of hydration from said hydrated compound without causing substantial decomposition of said chloroammelide moiety.

12. A process defined by claim 11 wherein R is Na, Y is Cl, and said removing is carried out at a temperature of at least about 80° C.
13. A process defined by claim 12 wherein said temperature is at least about 90° C.
14. A process defined by claim 12 wherein said temperature is at least about 104° C.
15. A process defined by claim 12 wherein said temperature is at least about 118° C.

16. A process defined by claim 11 wherein R is Na, Y is H, and said removing is carried out at a temperature of at least about 72° C.

17. A process defined by claim 16 wherein said temperature is at least about 90° C.

18. A process defined by claim 11 wherein R is K, Y is Cl, and said removing is carried out at a temperature of at least about 110° C.

19. A process defined by claim 11 wherein R is K, Y is H, and said removing is carried out at a temperature of at least about 110° C.

20. A process defined by claim 11 wherein R is H, and said removing is carried out at a temperature of at least about 87° C.

* * * * *